US011926604B2

(12) United States Patent
Rivkees

(10) Patent No.: US 11,926,604 B2
(45) Date of Patent: Mar. 12, 2024

(54) MYELINATION STIMULATOR COMPOUNDS, AND METHODS OF TREATMENT

(71) Applicant: UNIVERSITY OF FLORIDA RESEARCH FOUNDATION, INCORPORATED, Gainesville, FL (US)

(72) Inventor: Scott A. Rivkees, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 720 days.

(21) Appl. No.: 17/054,600

(22) PCT Filed: May 10, 2019

(86) PCT No.: PCT/US2019/031746
§ 371 (c)(1),
(2) Date: Nov. 11, 2020

(87) PCT Pub. No.: WO2019/217834
PCT Pub. Date: Nov. 14, 2019

(65) Prior Publication Data
US 2021/0188792 A1   Jun. 24, 2021

Related U.S. Application Data

(60) Provisional application No. 62/670,221, filed on May 11, 2018.

(51) Int. Cl.
*C07D 285/24* (2006.01)
*A61P 25/28* (2006.01)

(52) U.S. Cl.
CPC ............ *C07D 285/24* (2013.01); *A61P 25/28* (2018.01)

(58) Field of Classification Search
CPC ............................... C07D 285/24; A61P 25/28
USPC ..................................................... 514/223.2
See application file for complete search history.

(56) References Cited

U.S. PATENT DOCUMENTS

| 6,242,443 B1 | 6/2001 | Pirotte et al. |
| 2004/0043987 A1 | 3/2004 | Gouliaev et al. |
| 2006/0189603 A1 | 8/2006 | Garvey et al. |
| 2009/0163545 A1 | 6/2009 | Goldfarb |

FOREIGN PATENT DOCUMENTS

| WO | 2009049018 A1 | 4/2009 |
| WO | 2010111518 A1 | 9/2010 |

OTHER PUBLICATIONS

Bell et al JOC 1964, 29(11) 3206-3209 (Year: 1964).*
PCT/US2019/031746 PCT Search Report and Written Opinion, dated Aug. 30, 2019, 13 pages.
Allin, Matthw et al., "Personality in Young Adults Who Are Born Preterm", Pediatrics, Feb. 2006, vol. 117, No. 2, pp. 309-316.
Allin, M. et al., "Cognitive maturation in preterm and term born adolescents", J Neurol Neurosurg Psychiatry, 2008, vol. 79, pp. 381-386.
Back, Stephen A. et al., "Pathophysiology of Glia in Perinatal White Matter Injury", Glia, 2014, vol. 62, pp. 1790-1815.
Back, Stephen A., "Recent advances in human perinatal white matter injury", Progress in Brain Research, 2001, vol. 132, pp. 131-147.
Back, Stephen A. et al., "Brain Injury in Premature Neonates: A Primary Cerebral Dysmaturation Disorder?", Ann Neurol, 2014, vol. 75, pp. 469-486.
Back, Stephen A. et al., "Maturation-Dependent Vulnerability of Oligodendrocytes to Oxidative Stress-Induced Death Caused by Glutathione Depletion", The Journal of Neuroscience, Aug. 15, 1998, vol. 18, No. 16, pp. 6241-6253.
Back, Stephen A. et al., "Late Oligodendrocyte Progenitors Coincide with the Developmental Window of Vulnerability for Human Perinatal White Matter Injury", The Journal of Neuroscience, Feb. 15, 2001, vol. 21, 14, pp. 1302-1312.
Back, Stephen A. et al., "Arrested Oligodendrocyte Lineage Progression During Human Cerebral White Matter Development: Dissociation Between the Timing of Progenitor Differentiation and Myelinogenesis", Journal of Neuropathology and Experimental Neurology, Feb. 2002, vol. 61, No. 2, pp. 197-211.
Back, Stephen A. et al., "Emerging Concepts in Periventricular White Matter Injury", Semin Perinatol, 2004, vol. 28, pp. 405-414.
Back, Stephen A., "Cerebral White and Gray Matter Injury in Newborns", Clin Perinatol, 2014, vol. 41, pp. 1-24.
Back, Stephen A., "White matter injury in the preterm infant: pathology and mechanisms", Acta Neuropathol, 2017, vol. 134, pp. 331-349.
Back, Stephen A. et al., "Brain Injury in the Preterm Infant: New Horizons for Pathogenesis and Prevention", Pediatric Neurology, 2015, vol. 53, pp. 185-192.
Back, Stephen A., "Perinatal White Matter Injury: The Changing Spectrum of Pathology and Emerging Insights Into Pathogenetic Mechanisms", Mental Retardation and Developmental Disabilities Research Reviews, 2006, vol. 12, pp. 129-140.
Back, Stephen A. et al., "Protective Effects of Caffeine on Chronic Hypoxia-Induced Perinatal White Matter Injury", Ann Neurol, 2006, vol. 60, pp. 696-705.
Bayless, Sarah et al., "Executive functions in school-age children born very prematurely", Early Human Development, 2007, vol. 83, pp. 247-254.
Buser, Joshua R. et al., "Arrested Preoligodendrocyte Maturation Contributes to Myelination Failure in Premature Infants", American Neurological Association, 2012, vol. 71, pp. 93-109.

(Continued)

*Primary Examiner* — Yevgeny Valenrod
(74) *Attorney, Agent, or Firm* — Timothy H. Van Dyke; WOLTER, VAN DYKE, DAVIS, PLLC

(57) ABSTRACT

The invention is directed towards compounds, methods of stimulating myelination, stimulating proliferation of oligodendrocytes (OLs) or stimulating oligodendrocyte precursor cells and methods of treating diseases, disorders or symptoms thereof.

13 Claims, 4 Drawing Sheets

(56) References Cited

OTHER PUBLICATIONS

Constable, R. Todd et al., "Prematurely Born Children Demonstrate White Matter Microstructural Differences at 12 Years of Age, Relative to Term Control Subjects: An Investigation of Group and Gender Effects", Pediatrics, 2008, vol. 121, pp. 306-316.
Craig Andrew et al., "Quantitative analysis of perinatal rodent oligodendrocyte lineage progression and its correlation with human", Experimental Neurology, 2003, vol. 181, pp. 231-240.
Dimitropoulos, Anastasia et al., "Brain injury and development in newborns with critical congenital heart disease", American Academy of Neurology, Jul. 16, 2013, vol. 81, pp. 241-248.
Dugas, Jason C. et al., "Functional Genomic Analysis of Oligodendrocyte Differentiation", The Journal of Neuroscience, Oct. 25, 2006, vol. 26, No. 43, pp. 10967-10983.
Edgin, Jamie O. et al., "Executive functioning in preschool children born very preterm: Relationship with early white matter pathology", Journal of the International Neuropsychological Society, 2008, vol. 14, pp. 90-101.
Fogal, Birgit et al., "Diazoxide Promotes Oligodendrocyte Precursor Cell Proliferation and Myelination", PLoS ONE, May 2010, vol. 5, Issue 5, 9 pages.
Garg, A.L. et al., "Two Proliferative Stages of the Oligodendrocyte Lineage (A2B5+O4- and O4+GalC-) under different Mitogenic Control", Neuron, Nov. 1990, vol. 5, pp. 615-625.
Hoyert, Donna L. et al., "Annual Summary of Vital Statistics: 2004", Pediatrics, 2006, vol. 117, pp. 168-183.
Jones, Laurie J. et al., "Sensitive determination of cell No. using the CyQUANT cell proliferation assay", Journal of Immunological Methods, 2001, vol. 254, pp. 85-98.
Kesler, Shelli R. et al., "Brain Volume Reductions within Multiple Cognitive Systems in Male Preterm Children at Age Twelve", The Journal of Pediatrics, Apr. 2008, 513-520.e1.
Kinney, Hannah C. et al., "Human Oligodendroglial Development: Relationship to Periventricular Leukomalacia", Seminars in Pediatric Neurology, Sep. 1998, vol. 5, No. 3, pp. 180-189.
Kuban, Karl et al., "White matter disorders of prematurity: Association with intraventricular hemorrhage and ventriculomegaly", The Journal of Pediatrics. May 1999, pp. 539-546.
Limperopoulos, Catherine et al., "Does Cerebellar Injury in Premature Infants Contribute to the High Prevalence of Long-term Cognitive, Learning, and Behavioral Disability in Survivors?", Pediatrics, Sep. 2007, vol. 120, No. 3, pp. 584-593.
Limperopoulos, Catherine et al., "Late Gestation Cerebellar Growth Is Rapid and Impeded by Premature Birth", Pediatrics, 2005, vol. 115, pp. 688-695.
Ment, Laura R. et al., "Association of chronic sublethal hypoxia with ventriculomegaly in the developing rat brain", Developmental Brain Research, 1998, vol. 111, pp. 197-203.
Murata, Akira et al., "Rodent brain slice model for the study of white matter injury", The Journal of Thoracic and Cardiovascular Surgery, Dec. 2013, vol. 146, No. 6, pp. 1526-1533.e1.
Nishiyama A. et al., "Co-Localization of NG2 Proteoglycan and PDGF Receptor on O2A Progenitor Cells in the Developing Rat Brain", Journal of Neuroscience Research, 1996, vol. 43, pp. 299-314.
Nosarti, Chiara et al., "Grey and white matter distribution in very preterm adolescents mediates neurodevelopmental outcome", Brain, 2008, vol. 131, pp. 205-217.
Othman, Timothy et al., "Oligodendrocytes Express Functional A1 Adenosine Receptors That Stimulate Cellular Migration", Glia, 2003, vol. 44, pp. 166-172.
Perlman, Jeffrey M., "White matter injury in the preterm infant: an important determination of abnormal neurodevelopment outcome", Early Human Development, 1998, vol. 53, pp. 99-120.
Rezaie, Payam et al., "Periventricular leukomalacia, inflammation and white matter lesions within the developing nervous system", Neuropathology, 2002, vol. 22, pp. 106-132.
Riddle, Art et al., "Histopathological Correlates of Magnetic Resonance Imaging-Defined Chronic Perinatal White Matter Injury", Ann Neurol, 2011, vol. 70, pp. 493-507.
Rushing, Susan et al., "Preterm Birth: A Cost Benefit Analysis", Semin Perinatol, 2004, vol. 28, pp. 444-450.
Salmaso, Natalina et al., "Neurobiology of premature brain injury", Nature Neuroscience, Mar. 2014, vol. 17, No. 3, pp. 341-346.
Scafidi, Joseph et al., "Intranasal epidermal growth factor treatment rescues neonatal brain injury", Nature, Feb. 2014, vol. 506, 19 pages.
Scolding, N.J. et al., "Identification of A2B5-Positive Putative Oligodendrocyte Progenitor Cells and A2B5-Positive Astrocytes in Adult Human White Matter", Neuroscience, 1999, vol. 89, No. 1, pp. 1-4.
Segovia, Kristen N. et al., "Arrested Oligodendrocyte Lineage Maturation in Chronic Perinatal White Matter Injury", Ann Neurol, 2008, vol. 63, pp. 520-530.
Skoff, Robert P. et al., "Postmitotic Oligodendrocytes Generated During Postnatal Cerebral Development Are Derived From Proliferation of Immature Oligodendrocytes", Glia, 1994, vol. 12, pp. 12-23.
Thompson, Deanna K. et al., " MR-Determined Hippocampal Asymmetry in Full-Term and Preterm Neonates", Hippocampus, 2009, vol. 19, pp. 118-123.
Thompson, Deanna K. et al., "Neonate Hippocampal Volumes: Prematurity, Perinatal Predictors, and 2-Year Outcome", Ann Neurol, 2008, vol. 63, pp. 642-651.
Tilborg, Erik Van et al., "Origin and dynamics of oligodendrocytes in the developing brain: Implications for perinatal white matter injury", Glia, 2018, vol. 66, pp. 221-238.
Tilborg, Erik Van et al., "Impaired oligodendrocyte maturation in preterm infants: Potential therapeutic targets", Progress in Neurobiology, 2016, vol. 136, pp. 28-49.
Turner, Christopher P. et al., "A1 adenosine receptors mediate hypoxia-induced ventriculomegaly", PNAS, Sep. 30, 2003, vol. 100, No. 20, pp. 11718-11722.
Turner, Christopher P. et al., "AI adenosine receptor activation induces ventriculonegaly and white matter loss", Developmental Neuroscience, Jul. 2002, vol. 13, No. 2, pp. 1199-1204.
Uehara, Hisakazu et al., "A new model of white matter injury in neonatal rats with bilateral carotid artery occlusion", Brain Research, 1999, vol. 837, pp. 213-220.
Volpe, Joseph J., " Neurobiology of Preventricular Leukomalacia in Premature Infant", Pediatric Research, 2001, vol. 50, No. 5, pp. 553-562.
Volpe, Joseph J., " Brain injury in premature infants: a complex amalgam of destructive and developmental disturbances", Lancet Neurol, 2009, vol. 8, pp. 110-124.
Walshe, M. et al., "Psychiatric disorder in young adults born very preterm: Role of family history", European Psychiatry, 2008, vol. 23, pp. 527-531.
Warrington, A.E. et al., "Stage Specific, (O4+GalC-) Isolated Oligodendrocyte Progenitors Produce MBP+Myelin in vivo", Dev Neurosci, 1992, vol. 14, pp. 93-97.
Warrington, A.E. et al., "Proliferation and Differentiation of O4+ Oligodendrocytes in Postnatal Rat Cerebellum: Analysis in Unfixed Tissue Slices Using Anti-Glycolipid Antibodies", Journal of Neuroscience Research, 1992, vol. 33, pp. 338-353.
Wilson-Costello, Deanne et al., "Improved Survival Rates with Increased Neurodevelopmental Disability for Extremely Low Birth Weight Infants in the 1990s", Pediatrics, Apr. 2005, vol. 115, No. 4, pp. 997-1003.
Woodward, Lianne J. et al., "Object working memory deficits predicted by early brain injury and development in the preterm infant", Brain, 2005, vol. 128, pp. 2578-2587.
Yan, Henglin et al., "Hepatocyte Growth Factor Stimulates the Proliferation and Migration of Oligodendrocyte Precursor Cells", Journal of Neuroscience Research, 2002, vol. 69, pp. 597-606.
Yan, Henglin et al., "Hypoglycemia influences oligendrocyte development and myelin formation", NeuroReport, Jan. 2006, vol. 17, No. 23, pp. 55-59.

(56) References Cited

OTHER PUBLICATIONS

Zhu, Ying et al., "Diazoxide promotes oligodendrocyte differentiation in neonatal brain in normoxia and chronic sublethal hypoxia", Brain Research, 2014, vol. 1586, pp. 64-72.
EP search report, EP19799728.1, dated Dec. 3, 2021, 6 pages.

* cited by examiner

MYELINATION STIMULATOR COMPOUNDS, AND METHODS OF TREATMENT

RELATED APPLICATIONS

This Application claims the benefit under 35 U.S.C. § 119(e) of the filing date of U.S. Provisional Application Ser. No. 62/670,221, filed May 11, 2018, entitled "MYELINATION STIMULATOR COMPOUNDS, AND METHODS OF TREATMENT", the entire contents of which is incorporated by reference herein.

STATEMENT OF RIGHTS TO INVENTIONS MADE UNDER FEDERALLY SPONSORED RESEARCH

This invention was made with government support under NS095475 awarded by National Institutes of Health. The government has certain rights in the invention.

BACKGROUND

Periventricular white matter injury in premature infants (PWMI; also referred to as diffuse white matter injury, or leukoencephalopathy of prematurity) is a neurological disorder characterized by reduction of white matter in periventricular and other brain regions[1-10] Up to 30% of preterm infants manifest some form of PWMI, making it the most common form of brain injury affecting premature infants[3,5-7,11].

PWMI is associated with attention, behavioral, and socialization deficits[12]. Such deficits include impairment in intelligence, object working memory, various executive functions, impulse control, and some characteristics of autism[13-25] Highlighting the magnitude of PWMI, each year in the United States more than 400,000 infants are born prematurely, with 150,000 born before 32-week, post-conception age[26]. Of the 150,000 infants born annually at risk for PWMI, about 25,000 children per year will develop PWMI. Worldwide, 1,000,000 infants will be born annually at risk for PWMI, and about 250,000 children per year will develop PWMI[10,27,28]. It is estimated the lifetime care costs for infants who develop cerebral palsy due to PWMI exceeds $2.0 million per infant[27].

Despite the wide prevalence of PWMI and the considerable morbidity associated with it, no direct treatments are available to either treat or prevent the white matter injury that these infants sustain. Recent studies show that caffeine and epidermal growth factor may mitigate this condition in animals 29,30. However, none is fully protective. Thus, finding a treatment for PWMI is of major public health importance and of great commercial potential.

Provided herein are compounds, compositions, and methods of use that are useful to address significant unmet need of patients afflicted with disorders associated with oligodendrocyte stimulation and differentiation, myelination, and symptoms thereof.

BRIEF SUMMARY OF THE INVENTION

The invention is directed towards compounds (e.g., any of those delineated herein), methods of stimulating myelination, and methods of treating diseases, disorders or symptoms thereof. The methods can comprise the compounds herein.

It is understood that the embodiments of the invention discussed below with respect to the preferred variable selections can be taken alone or in combination with one or more embodiments, or preferred variable selections, of the invention, as if each combination were explicitly listed herein.

In one aspect, provided are compounds of Formula I:

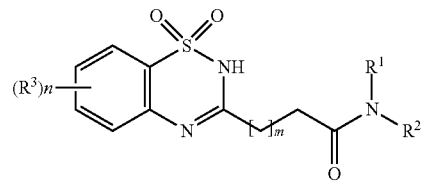

or pharmaceutically acceptable salts, solvates, or hydrates, thereof, wherein:
- each $R^1$ is independently H, alkyl substituted with 1-3 independent $R^4$;
- each $R^2$ is independently alkyl substituted with 1-3 independent $R^4$; or
- $R^1$ and $R^2$ taken together with the nitrogen atom to which they are attached form a heterocycloalkyl ring having 1, 2, or 3 heteroatoms selected from N, O, and S, wherein the heterocycloalkyl ring may be optionally substituted with 1-3 independent $R^4$;
- each $R^3$ is independently alkyl, alkoxy, amino, halo, $C(O)R^5$, $C(O)OR^5$, $SR^5$, or $NR^5R^6$;
- each $R^4$ is independently alkoxy, or aryl optionally substituted with 1-3 independent $R^7$;
- each $R^5$ is independently H, or alkyl;
- each $R^6$ is independently H, or alkyl;
- each $R^7$ is independently alkyl, alkoxy, amino, halo, $C(O)R^5$, $C(O)OR^5$, $SR^5$, $S(O)_2R^5$, $S(O)_2NR^5R^6$, or $NR^5R^6$;
- n is 0, 1, 2, 3, or 4;
- m is 1, 2, 3, or 4.

In another aspect the compounds are those of Formula I, or pharmaceutically acceptable salts, solvates, or hydrates, thereof, wherein:
- each $R^1$ is independently H;
- each $R^2$ is independently alkyl substituted with 1-3 independent $R^4$;
- n is 0, and m is 1.

In another aspect the compounds are those of Formula I, or pharmaceutically acceptable salts, solvates, or hydrates, thereof, wherein:
- each $R^1$ is independently H;
- each $R^2$ is independently alkyl substituted with 1-3 independent $R^4$;
- n is 0, and m is 1;
- each $R^4$ is independently alkoxy.

In another aspect the compounds are those of Formula I, or pharmaceutically acceptable salts, solvates, or hydrates, thereof, wherein:
- each $R^1$ is independently H;
- each $R^2$ is independently alkyl substituted with 1-3 independent $R^4$;
- n is 0, and m is 2.

In another aspect the compounds are those of Formula I, or pharmaceutically acceptable salts, solvates, or hydrates, thereof, wherein:
- each $R^1$ is independently H;
- each $R^2$ is independently alkyl substituted with 1-3 independent $R^4$;

n is 0, and m is 2;

each $R^4$ is independently alkoxy.

In another aspect the compounds are those of Formula I, or pharmaceutically acceptable salts, solvates, or hydrates, thereof, wherein:

$R^1$ and $R^2$ taken together with the nitrogen atom to which they are attached form a heterocycloalkyl ring having 1 or 2 heteroatoms selected from N, O, and S, wherein the heterocycloalkyl ring may be optionally substituted with 1-3 independent $R^4$;

n is 0, and m is 1.

In another aspect the compounds are those of Formula I, or pharmaceutically acceptable salts, solvates, or hydrates, thereof, wherein:

$R^1$ and $R^2$ taken together with the nitrogen atom to which they are attached form a heterocycloalkyl ring having 1 or 2 heteroatoms selected from N, O, and S, wherein the heterocycloalkyl ring may be optionally substituted with 1-3 independent $R^4$;

n is 0, and m is 1;

each $R^4$ is independently aryl optionally substituted with 1-3 independent $R^7$;

each $R^7$ is independently alkyl, alkoxy, amino, halo, $C(O)R^5$, $C(O)OR^5$, $SR^5$, $S(O)_2R^5$, $S(O)_2NR^5R^6$, or $NR^5R^6$.

In other aspects the compounds are those of Formula I, or pharmaceutically acceptable salts, solvates, or hydrates, thereof:

wherein n is 0, and m is 1;

wherein n is 0, and m is 2.

In other aspects the compounds of the invention are:

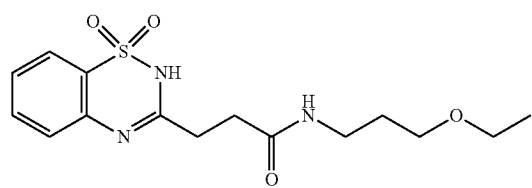

K261-0298
3-(1,1-dioxido-2H-benzo[e][1,2,4]thiadiazin-3-yl)-N-
(3-ethoxypropyl)propanamide

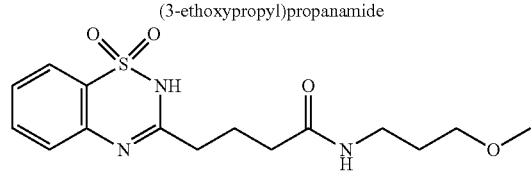

K261-0186
4-(1,1-dioxido-2H-benzo[e][1,2,4]thiadiazin-3-yl)-N-
(3-methoxypropyl)butanamide

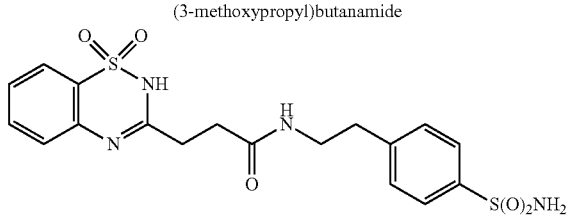

K261-0288
3-(1,1-dioxido-2H-benzo[e][1,2,4]thiadiazin-3-yl)-N-
(4-sulfamoylphenethyl)propanamide

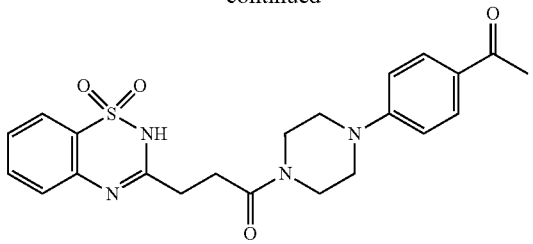

K261-0310
1-(4-(4-acetylphenyl)piperazin-1-yl)-3-(1,1-
dioxido-2H-benzo[e][1,2,4]thiadiazin-3-yl)
propane-1-one or pharmaceutically acceptable salts, solvates, or hydrates, thereof.

In another aspect, provided are pharmaceutical compositions comprising a compound delineated herein (e.g., the compound of Formula I or pharmaceutically acceptable salts, solvates, or hydrates, thereof) and a pharmaceutically acceptable carrier.

In another aspect, provided are methods of stimulating myelination (e.g., treating hypomyelination), comprising administering to said subject in need thereof, an effective amount of a compound delineated herein or pharmaceutical composition delineated herein (e.g., Formula I, or pharmaceutically acceptable salts, solvates, or hydrates, thereof).

In another aspect, provided are methods of stimulating proliferation of oligodendrocytes (OLs) or ligodendrocyte precursor cells, comprising administering to said subject in need thereof, an effective amount of a compound delineated herein or pharmaceutical composition delineated herein (e.g., Formula I, or pharmaceutically acceptable salts, solvates, or hydrates, thereof).

In another aspect, provided are methods of reducing ventriculomegaly, comprising administering to said subject in need thereof, an effective amount of a compound delineated herein or pharmaceutical composition delineated herein (e.g., Formula I, or pharmaceutically acceptable salts, solvates, or hydrates, thereof).

In another aspect, provided are methods of treating a subject suffering from or susceptible to a disorder or disease, wherein the subject has been identified as in need of treatment for the disorder or disease, comprising administering to said subject in need thereof, an effective amount of a compound delineated herein or pharmaceutical composition delineated herein (e.g., Formula I, or pharmaceutically acceptable salts, solvates, or hydrates, thereof), such that said subject is treated for said disorder.

In another aspect the subject is an animal other than a human.

The methods herein include those wherein the disease or disorder is any described herein, including, periventricular white matter injury (PWMI; also referred to as diffuse white matter injury, or leukoencephalopathy), myelination disorders, abnormal PreOL proliferation, abnormal PreOL differentiation, symptoms associated with PWMI (e.g., attention, behavioral, and socialization deficits, impairment in intellegence, object working memory, various executive functions, impulse control, or some characteristics of autism), cerebral palsey.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which:

FIG. 1. depicts stages of OL differentiation.

FIG. 2. A. Myelin basic protein labeling (green) of brain slices incubated with compounds for 5 days in culture. *, p<0.05 vs vehicle. ANOVA. Data shown are representative at least 3 slices per treatment group per study, in at least 3 separate studies. (B) Vehicle, (C) K-261-0298. Note increased labeling. These data show that K-261-0298 stimulates myelination in vitro.

FIG. 3. Myelin basic protein (MBP), O4 and O1 labeling of coronal forebrain at level of corpus callosum (cc) of newborn mice treated with vehicle or drug (K261-298) from P2 to P12 in room air. Data shown are representative of at least 5 pups per treatment group. cc, corpus callosum. Scale bar=100 um. Note that K-261-0298 is associated with a reduction in O4 expression (p<0.02; ANOVA) and an increase in O1 labeling (p<0.02; ANOVA), showing an increase in OL lineage maturation.

FIG. 4: Reduction in ventriculomegaly in hypoxia-exposed mouse treated with K261-0298 (100 mg/kg/d, P2-P12) or vehicle treated. Darkfield, hemi-coronal sections at the same brain levels shown. Data shown are representative of 4 pups per treatment group. Arrow depict lateral ventricles. ac, anterior commisure. Note smaller ventricle size in the drug-treated pup. Scale bar=500 um.

DETAILED DESCRIPTION

Definitions

Figure 1A:
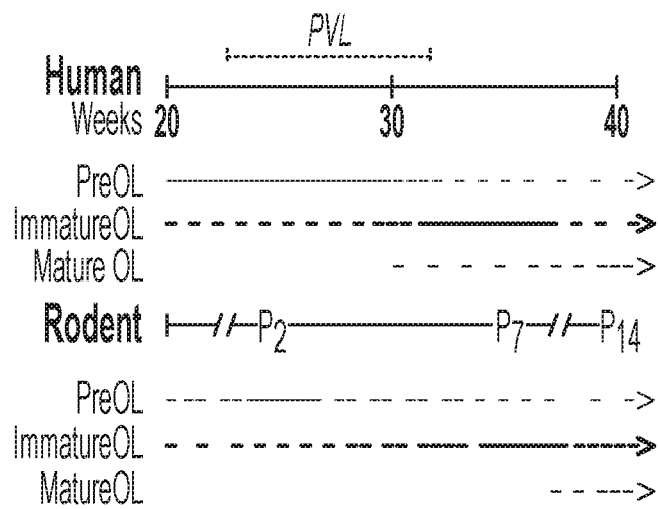
FIG. 1A. Diagram comparing features of human versus rodent oligodendrocyte (OL) lineage progression.

In order that the invention may be more readily understood, certain terms are first defined here for convenience.

As used herein, the term "treating" a disorder encompasses ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes blocking, inhibiting, attenuating, modulating, reversing the effects of and reducing the occurrence of e.g., the harmful effects of a disorder.

As used herein, the term "preventing" a disorder encompasses stopping initiation of, or stopping the arising of the disorder and/or symptoms or conditions that may cause the disorder. The terms "preventing" and "prevention" refer to a method of effectual hindrance of a disease and/or its attendant symptoms.

As used herein, "inhibiting" encompasses preventing, reducing and halting progression.

As used herein, "activating" encompasses permitting, increasing and enhancing progression.

As used herein, "enriched" encompasses greater or increased amounts of a material or desired or active compound or agent relative to its natural or other reference state.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the present disclosure are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human. In certain embodiments, the subject is a human child, a human infant, or a human premature infant.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The phrases "systemic administration," "administered systemically", "peripheral administration" and "administered peripherally" as used herein mean the administration of a compound(s), drug or other material, such that it enters the patient's system and, thus, is subject to metabolism and other like processes.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds (e.g., isolated compounds) of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

The present invention also contemplates solvates (e.g., hydrates) of a compound of herein, compositions thereof, and their use in the treatment of disease or symptoms thereof as described herein. As used herein, "solvate" refers to the physical association of a compound of the invention with one or more solvent or water molecules, whether organic or inorganic. In certain instances, the solvate is capable of isolation, for example, when one or more solvate molecules are incorporated in the crystal lattice of the crystalline solid.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

This invention is directed towards compounds, compositions, and methods of treating and/or preventing diseases and disorders by use of the compounds or compositions delineated herein.

In other aspects, the invention provides a method of treating and/or preventing a disease, disorder, or symptom thereof in a subject, comprising administering to the subject any compound herein. In another aspect, the compound is administered in an amount and under conditions sufficient to ameliorate the disease, disorder, or symptom thereof in a subject.

In certain embodiments, the subject is a mammal, preferably a primate or human.

In another embodiment, the invention provides a method as described above, wherein the effective amount of the compound ranges from about 0.005 µg/kg to about 500 mg/kg, preferably about 0.1 mg/kg to about 500 mg/kg, more preferably about 10 mg/kg to about 500 mg/kg of body weight.

In other embodiments, the invention provides a method as described above wherein the effective amount of the compound, ranges from about 1.0 nM to about 500 µM. In another embodiment, the effective amount ranges from about 100 nM to about 100 µM.

In other embodiments, the invention provides a method as described above wherein the effective amount of the compound, ranges from about 0.1 mg/ml to about 1000 mg/ml. In certain embodiments, the effective amount ranges from about 1.0 mg/ml to about 500 mg/ml. In another embodiment, the effective amount ranges from about 1.0 mg/ml to about 100 mg/ml.

In another embodiment, the invention provides a method as described above, wherein the compound is administered intravenously, intramuscularly, subcutaneously, intracerebroventricularly, orally, ocularly, or topically.

In other embodiments, the invention provides a method as described above, wherein the compound is administered alone or in combination with one or more other therapeutic agents.

Another object of the present invention is the use of a compound as described herein (e.g., of any formulae herein) in the manufacture of a medicament for use in the treatment and/or prevention of a disorder or disease described herein. Another object of the present invention is the use of a compound as described herein (e.g., of any formulae herein) for use in the treatment and/or prevention of a disorder or disease described herein.

Pharmaceutical Compositions

In one aspect, the invention provides a pharmaceutical composition comprising the compound of any of the formulae herein and a pharmaceutically acceptable carrier.

In one embodiment, the invention provides a pharmaceutical composition wherein the compound is selected from the group consisting of:
a) 3-(1,1-dioxido-2H-benzo[e][1,2,4]thiadiazin-3-yl)-N-(3-ethoxypropyl)propanamide (1) [K261-0298];
b) 4-(1,1-dioxido-2H-benzo[e][1,2,4]thiadiazin-3-yl)-N-(3-methoxypropyl)butanamide (2) [K261-0186];
c) 2,6-dibromo-1,1,4a-trimethyl-2,3,4,4a,9,9a-hexahydro-1H-xanthen-7-ol 3-(1,1-dioxido-2H-benzo[e][1,2,4]thiadiazin-3-yl)-N-(4-sulfamoylphenethyl)propanamide (3) [K261-0288];
d) 1-(4-(4-acetylphenyl)piperazin-1-yl)-3-(1,1-dioxido-2H-benzo[e][1,2,4]thiadiazin-3-yl)propan-1-one, (4) [K261-0310]; and
e) pharmaceutically acceptable salts thereof,
and a pharmaceutically acceptable carrier.

In another embodiment, the invention provides a pharmaceutical composition further comprising an additional therapeutic agent.

In one aspect, the invention provides a kit comprising an effective amount of a the compound, in unit dosage form, together with instructions for administering the compound to a subject suffering in need of stimulating myelination (e.g., treating hypomyelination), stimulating proliferation of oligodendrocytes (OLs), or stimulating oligodendrocyte precursor cells, comprising administering to said subject in need thereof, an effective amount of a compound or pharmaceutical composition of Formula I (or pharmaceutically acceptable salts, solvates, or hydrates, thereof).

In one aspect, the invention provides a kit comprising an effective amount of a compound, or composition thereof, in unit dosage form, together with instructions for administering the compound to a subject suffering from or susceptible to a disease or disorder, including periventricular white matter injury (PWMI; also referred to as diffuse white matter injury, or leukoencephalopathy), myelination disorders, abnormal PreOL proliferation, abnormal PreOL differentiation, symptoms associated with PWMI (e.g., attention, behavioral, and socialization deficits, impairment in intellegence, object working memory, various executive functions, impulse control, or some characteristics of autism), or cerebral palsey.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral, ocularly, or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

Topical administration of the pharmaceutical compositions of this invention is especially useful when the desired treatment involves areas or organs readily accessible by topical application. For topical application topically to the skin, the pharmaceutical composition should be formulated with a suitable ointment, lotion, or cream containing the active components suspended or dissolved in a carrier. Carriers for topical administration of the compounds of this invention include, but are not limited to, water, phenoxyethanol, citric acid, phosphoric acid, succinic acid, steareth-20, potassium sorbate, methylparaben, propylparaben, butylparaben, ethylparaben, isobutylparaben, glyceryl stearate, dimethicone, capryl glycol, triethanolamine, maltodextrin, sorbic acid, ethylene brassylate, methyl linalool, isobutyl methyl tetrahydropyranol, phenonip, tocopheryl acetate, prodew 400, isododecane, pentylene glycol, capric/caprylic triglyceride, shea butter, cetyl alcohol, stearic acid, polysorbate 80, xanthan gum, C12-C15 alkyl benzoate, sunscreen agents, sodium cocoamphodiacetate, sodium methyl cocoyl taurate, lactose, talc, silicic acid, aluminum hydroxide, calcium silicates, polyamide powder, animal and vegetable fats, oils, waxes, paraffins (e.g., liquid paraffin, isoparaffin, soft paraffin), starch, tragacanth, cellulose derivatives, polyethylene glycols (e.g., polyethylene glycol, PEG-100 stearate, hexadecyl stearate, decyl stearate, isopropyl isostearate, stearyl stearate; aluminium stearate, glyceryl monostearate, PEG-12 dimethicone, polyethylene glycol (200-6000) mono- and di-fatty acid esters, PEG-300 or PEG-400), silicones, zinc oxide, propylene glycol, dipropylene glycol, polypropylene glycol, sorbitol, hydroxypropyl sorbitol, hexylene glycol, 1,3-butylene glycol, 1,3-butylene glycol monostearate, 1,3-butylene glycol distearate, 1,2,6-hexanetriol, ethoxylated glycerin, propoxylated glycerin, ethylhexylglycerin, xylitol, hexyl laurate, isohexyl laurate, isohexyl palmitate, ethylhexyl palmitate, isopropyl palmitate, decyl oleate, isodecyl oleate, diisopropyl adipate, diisohexyl adipate, dihexyldecyl adipate, diisopropyl sebacate, lauryl lactate, myristyl lactate, cetyl lactate, oleyl myristate, myristyl myristate, oleyl stearate, oleyl oleate; ethylene glycol mono- and di-fatty acid esters, diethylene glycol mono- and di-fatty acid esters, polyglycerol polyfatty esters, ethoxylated glyceryl monostearate, polyoxyethylene polyol fatty acid ester, sorbitan fatty acid esters (e.g., sorbitan isostearate, polyoxyethylene sorbitan fatty acid esters), cellulose polymers, carbomer polymers, carbomer derivatives, essential oils, terpenes, oxazoldines, surfactants, polyols, azone and azone derivatives, microcrystalline wax, wax esters such as beeswax, spermaceti, terol esters, cholesterol fatty acid esters, mineral oil, polyalphaolefins, petrolatum, polybutenes, lays (e.g., Montmorillonite, Hectorite, Laponite Bentonite), mica, silica, alumina, zeolites, sodium sulfate, sodium bicarbonate, sodium carbonate, calcium sulfate, fatty acid soaps, sodium lauryl sulfate, sodium lauryl ether sulfate, alkyl benzene sulfonate, mono- and di-alkyl acid phosphates, sarcosinates, taurates, sodium fatty acyl isethionate; dialkylamine oxide, betaines (e.g., betaine, cocamidopropyl betaine), vegetable oil (e.g., *arachis* oil, castor oil and the like), cetostearyl alcohol, wool-fat, non-ionic emulsifying agents, glycerol, cottonseed oil, groundnut oil, olive oil, sesame oil, soybean oil, cresols, benzyl alcohol, phenyllic alcohol, mannitol, sucrose, trehalose, glucose, raffinose, arginine, glycine, histidine, dextran, ethylene glycol, ethanol, and methanol. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Ocular administration of the pharmaceutical compositions of this invention is especially useful when the desired treatment involves areas or organs readily accessible by ocular application. For ocular application topically to the eyes, the pharmaceutical composition should be formulated with a suitable liquid, ointment, or cream containing the active components suspended or dissolved in a carrier. Carriers for ocular administration of the compounds of this invention include, but are not limited to, the aforementioned carriers for topical administration in addition to 1,2-dioleoyl-3-trimethylammonium-propane chloride (DOTAP), 1,2-distearoyl-SN-glycero-3-phosphocholine, alpha-tocopherol polyethylene glycol succinate, arginine octadecylamine, castor oil, chitosan, dextrose, gellan gum, hydroxypropylmethyl cellulose (HPMC), lecithins (egg and soybean), mannitol, oleylamine, poly(D, L-lactide-co-glycolide acid) (PLGA), Poloxamer 188, Poloxamer 407, Poloxamer CRL 1005, poly (F-caprolactone), poly (N-isopropylacrylamide (PNIPAAm), polyamidoamine (PAMAM), polyethylene glycol 200, polyethylene glycol 40 stearate, poly-hexyl-2-cyanoacrylate, poly-L-lysine (PLL), polymethacrylic acid, polysorbate 80, polyvinyl alcohol, propylene glycol, quaternary ammoniums, sodium alginate, sorbitol, stearylamine, tyloxapol, and water.

For topical administration, the active compound(s), extracts, enriched extracts, or prodrug(s) can be formulated as solutions, gels, lotions, ointments, creams, suspensions, and the like.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Examples

The present invention will now be demonstrated using specific examples that are not to be construed as limiting.

General Experimental Procedures

Compounds

Compounds of the invention are made using materials and procedures known to those of ordinary skill in the field of organic synthesis. Compounds can be made essentially using schemes as described herein, however it being understood that alternate synthetic routes, reagents, order of steps, and reaction conditions may be utilized to achieve manufacture of the compounds herein, and such alternatives are numerous and are described in known organic chemistry literature, and within the knowledge of one of ordinary skill in the art.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, Comprehensive Organic Transformations, VCH Publishers (1989) and subsequent editions thereof; T. W. Greene and P. G. M. Wuts, Protective Groups in Organic Synthesis, 3rd Ed., John Wiley and Sons (1999) and subsequent editions thereof; L. Fieser and M. Fieser, Fieser and Fieser's Reagents for Organic Synthesis, John Wiley and Sons (1994) and subsequent editions thereof; and L. Paquette, ed., Encyclopedia of Reagents for Organic Synthesis, John Wiley and Sons (1995) and subsequent editions thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Scheme I (variables correspond with those of Formula (I) as defined herein)

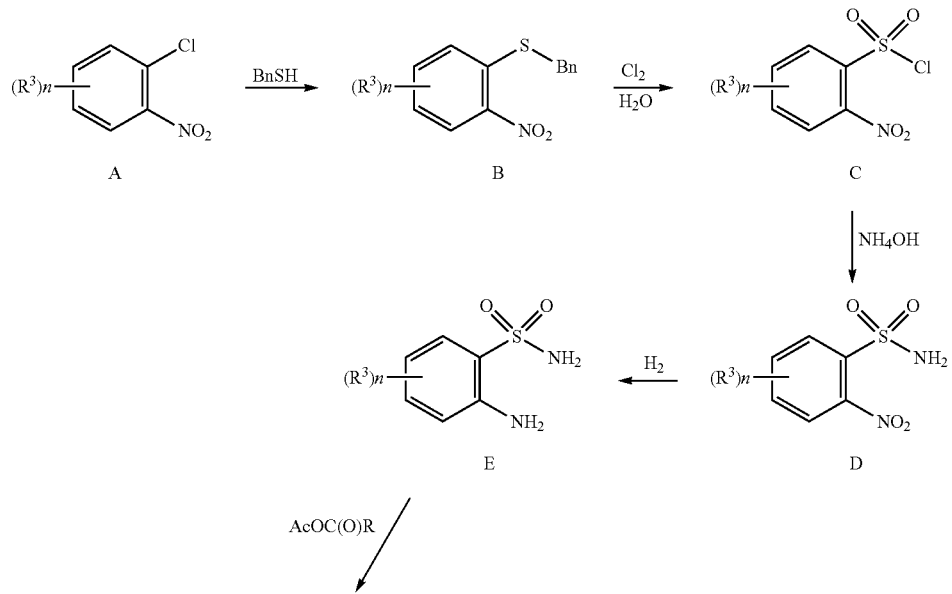

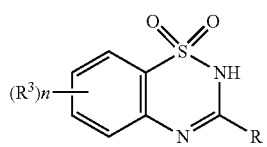

F

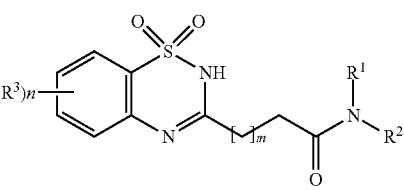

(I)

Compounds of the invention can be made, for example, essentially according to the protocol illustrated in Scheme I, wherein the group depicted as "R" is —(CH$_2$)m-CH$_2$—C(O)—NR$^1$R$^2$, or can be a suitably protected form of such group (protecting group and protecting/deprotecting chemical transformation technology being well established in the art; see, for example, T. W. Greene and P. G. M. Wuts, Protective Groups in Organic Synthesis, 3rd Ed., John Wiley and Sons (1999) and subsequent editions thereof, or can be a moiety that can be transformed to the desired "R" group using chemistry reagents, materials, and procedures known to those of ordinary skill in the field of organic synthesis, see, for example, aforementioned chemistry references.

The following compounds can be made essentially using the synthetic route above:

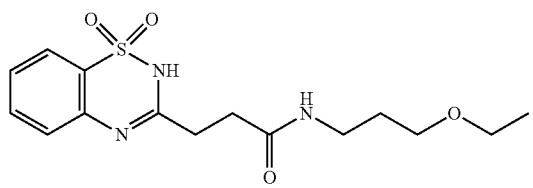

K261-0298
3-(1,1-dioxido-2H-benzo[e][1,2,4]thiadiazin-3-yl)-N-(3-ethoxypropyl)propanamide

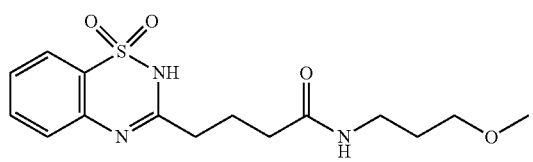

K261-0186
4-(1,1-dioxido-2H-benzo[e][1,2,4]thiadiazin-3-yl)-N-(3-methoxypropyl)butanamide

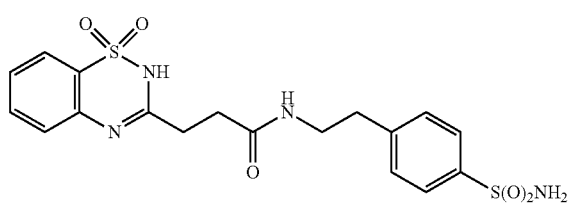

K261-0288
3-(1,1-dioxido-2H-benzo[e][1,2,4]thiadiazin-3-yl)-N-(4-sulfamoylphenethyl)propanamide

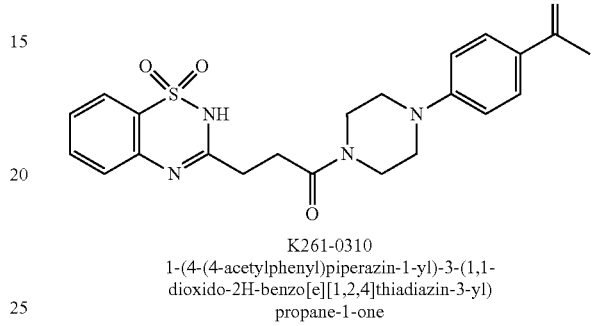

K261-0310
1-(4-(4-acetylphenyl)piperazin-1-yl)-3-(1,1-dioxido-2H-benzo[e][1,2,4]thiadiazin-3-yl)propane-1-one Myelination and Oligodendrocyte Development Reduced white matter is a major feature of PWMI[13,31-35] raising the possibility that there is abnormal development of oligodendrocytes (OLs)[57,10,36]. OL maturation involves a complex series of events during which progenitor cells undergo dramatic morphological and biochemical changes that lead to the formation of OLs that myelinate axons[34,35,37].

Four stages of OL differentiation are recognized, including early OL progenitors, late OL progenitors, immature OLs, and mature OLs (FIG. 1)[31,38,39] Early OL progenitor cells express the A2B5 antigen, the platelet-derived growth factor (PGF) receptor, and NG2 chondroitin sulfate proteoglycan[40,41] These cells differentiate into late oligodendrocyte progenitors. Late OL progenitor cells (PreOLs; also called oligodendrocyte precursor cells) express A2B5, O4 and NG2 surface antigen, but do not express O1 antigens[42-44] PreOLs also express Olig-2-labeled nuclei and the platelet-derived growth factor receptor-alpha (PGFR-alpha)[45]. PreOLs are mitotically active premyelinating cells, are migratory, and give rise to immature OLs, which express O1. In humans, PreOLs are present in the brains of premature infants from postconception ages 24 to 37 weeks[31], which correspond with the peak period of PWMI vulnerability[1,28,39].

An extensive body of literature shows that there are parallels between rodent and human OL development[34,35,39] Furthermore, in animals, PWMI-like features are induced by exposing neonates to hypoxia, hypoxia-ischemia, inflammation, or by reduction in cerebral blood flow[5-7,34,35,46,47], facilitating studies of OL maturation in these conditions.

Figure 1B:
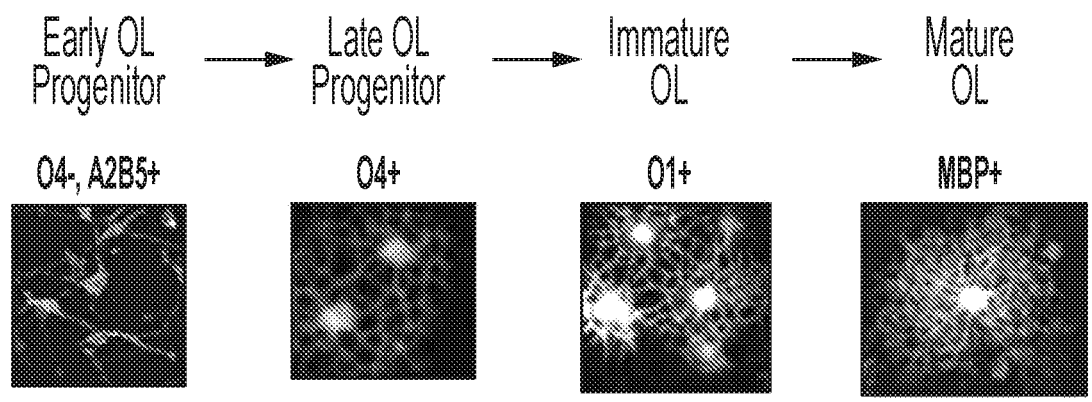
FIG. 1B. Cartoon of OL developmental stages showing stage marker antigens.

From postnatal days 2-7 (P2-7) in rodents, PreOLs predominate and correspond within the window of 20-28 weeks when PreOLs predominate in humans 39. This window overlaps with the high-risk period for PWMI that extends from 23 to 32 post-conception weeks 39. After P7 in rodents, immature OLs predominate, which overlaps with between 30 weeks and term birth (36-40 weeks) when human immature OLs peak. Thus, properly timed studies of rodent OLs can be used to mimic human OL development (FIG. 1; FIGS. 1A and 1B).

The leading concept in PWMI causation is that damage to or abnormal PreOL proliferation and/or differentiation depletes the brain of myelinating cells, resulting in white matter injury[3,9,28,34,35,48-52] (see supporting letter from Dr. Steven A. Back). Although there are no human clinical intervention studies of agents that specifically stimulate PreOLs, as such agents have not been tested. Recent experimental evidence shows that compounds that stimulate PreOLs differentiation and myelination improve neurobehavioral outcomes[30]. We also find that neonatal diazoxide therapy in a model of PWMI markedly improves myelination and reduces ventriculomegaly[53,54] and improves neurocognitive function. These results and observations indicate that it is possible to prevent white matter disease by developing therapeutic agents that stimulate OL proliferation and differentiation and myelination.

Biological Analysis

Compounds were tested for their ability to stimulate PreOL proliferation, as reported by us[54,57]. Primary cultures from rat were 98% PreOLs[58,60]. 10,000 cells were seeded at 25 uL/well volume in 24-well plates (BD Biosciences, Corning, PerkinElmer or NUNC). At least 4 positive (C+) and 4 negative (c−) controls were included on each plate. For positive controls, cells were treated with a combination of growth factors (10 ng/ml bFGF and 20 ng/ml PDGF). For negative controls, cells were treated with vehicle (DMEM+ media). For initial screening, we tested compounds at a final concentration of 1 uM.

To assess effects on cell proliferation, DNA content was assessed via fluorescent dye binding, using the commercially available NF CYQUANT® Assay Kit (Invitrogen, Carlsbad, CA), which has been validated for high throughput screening61. For each plate, the Z' factors were calculated, which is a parameter that evaluates the signal or screening window of a particular assay. Plates with Z' factors >0.5 were included in the final analysis (Positive and negative control mean signals ($\mu$) and standard deviations (a) were combined to calculate the Z' for each plate: 8 positive (c+) and 8 negative (c−) controls were included on each plate).

After initial screening, the compounds with the greatest effect on cell proliferation were selected for rescreening (each compound was tested on 3 independent plates). Compounds were tested side-by-side with diazoxide. Of the compounds evaluated, (K261-0288, K261-0298, K261-0186 and K261-0310) were 5-10 fold more potent than diazoxide in promoting proliferation.

Concentration-response studies were performed using concentrations between 1 pM and 1 uM. $EC_{50}$ values were −1 nM for K261-0186 and K261−0310 and −10 nM for K261-0288 and K261-0298. Considering the potency of diazoxide in stimulating white matter formation and attenuating PWMI in our previous studies[53,54] an increase in potency of up to 10-fold may potentially completely ameliorate this condition, which was achieved. These data show that the compounds herein potently stimulate PreOL proliferation greater than diazoxide.

Evaluation of Myelination in Brain Slices

Figure 2A:
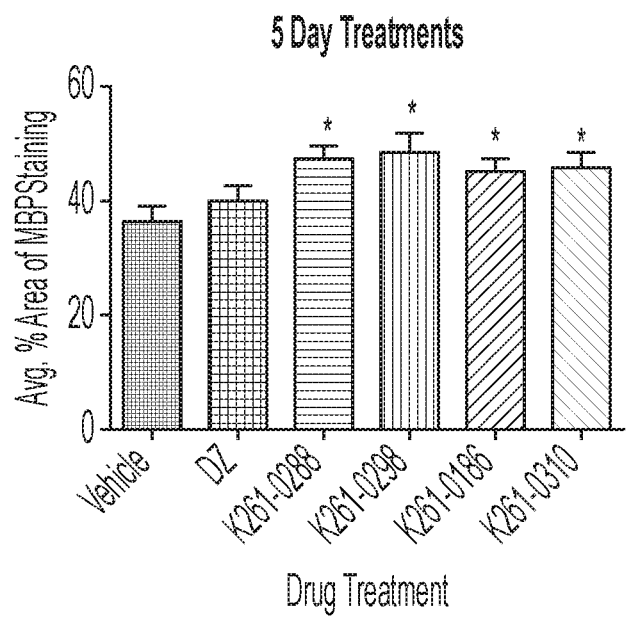
FIG. 2. depicts the effect of compounds on myelination stimulation.
Figure 2B:
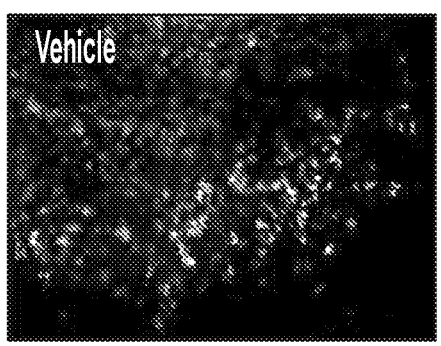
Figure 2C:
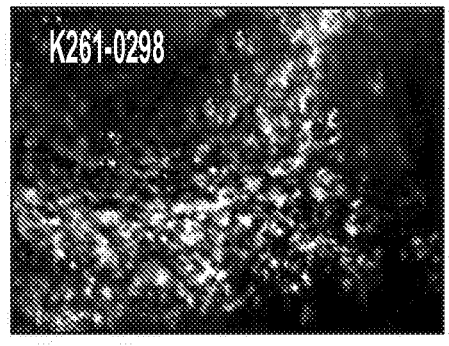

Before undertaking in vivo testing, we assessed the ability of the lead compounds to promote OL development and myelination using mouse brain slices, as reported[62,63]. Each compound and concentration was tested in triplicate, in at least three separate studies. Slices were collected at 1, 5, 9, or 13 days in vitro, fixed in 4% paraformaldehyde, and used for immunohistochemical staining. Slices were stained for markers of myelination (MBP; myelin basic protein; oligodendrocyte development (PGF-receptor, O1, Olig 2, O4) and markers of cell death (caspase-3), and DAPI to label all cells, as reported[62]. Data revealed that each of our lead compounds stimulated myelination more than diazoxide (FIG. 2), as there was at least a 25% increase in MBP staining versus vehicle for each compound. We also observed at least a 25% increase in the number of O1-labeled cells with each compound (data not shown; p<0.05) with each compound lending to increased numbers of PreOLs. These data show that Compound 1 [K261-0298] stimulates myelination in vitro.

In Vivo Toxicology

Critical in evaluating compounds for potential clinical use is assessment of in vivo safety. Following the above studies, we performed toxicology studies:

Dose-range and toxicity studies in mice. In consultation with UF veterinary staff and the IACUC committee, toxicity studies were performed. Based on the LD50 for our parent compound diazoxide (265-392 mg/kg), we assessed the approximate LD50 for these new compounds with a step wise approach using doses 5, 50, 100, and 400 mg/kg. Compounds were dissolved in 100% DMSO and diluted with 0.9% NaCl before injecting. The IP route (100-500 ul) was used to treat 8-10 week old female adults. We used females because in some studies they are more sensitive to toxins. Experiments were performed with the 2 compounds that had the largest effect on myelination in the brain slice cultures, including K261-0298 and K261-0310. Mice were treated with a single dose.

For K261-0298, the mice tolerated a single dose up to 400 mg/kg with no effect on weight or behavior. After 2 weeks, necropsies were done and no gross abnormalities were observed. Histopathological analysis did not reveal any evidence of cellular damage in any of the major organs examined. For K261-0310, the highest dose we were able to administer was 50 mg/kg, because the compound precipitated out of solution at higher concentrations. There were no adverse effects observed at the 50 mg/kg dose, either at the behavioral or gross necropsy levels.

Multiday studies. Because of its more favorable solubility properties allowing us to administer higher doses, we next performed multiday toxicity studies with the K261-0298. This study was performed at the 100 mg/kg dose for 10 days, and there were no adverse effects on animal behavior or weight loss over the 10-day experiment. Necropsies were performed on 5 controls and 5 K261-0298-treated mice and no gross malformations were observed. Histopathological analysis by a UF Veterinary Pathologist did not reveal evidence of damage in any major organs.

In addition, we also treated mouse pups starting on day P2 for ten days with 100 mg/kg/day K261-0298 or vehicle. We treated 47 pups from 7 different dams and all survived to the end of treatment without any differences in behavior or weight gain. We also evaluated for possible pulmonary hypertension. It does not appear that this compound induces pulmonary hypertension because all of our treated pups (N=47), juveniles (N=5), and adults (N=5) survived the ten days of treatment at 10-fold the dose given to humans. We did not observe any symptoms of pulmonary hypertension, shortness of breath, lung damage, including blood clots and bleeding, or cardiac hypertrophy.

Toxicokinetic Sample Collection: After the above studies, compound kinetics were examined. Male and female mice at approximately 60 days of age were used (n=8 mice per sex). Mice were given single i.p. injections of each of the doses identified above that do not result in toxicity. Samples were collected prior to dose and at 30 minutes, 2, 4, 8 and 24 hours after. Compound levels were determined by High Pressure Liquid Chromatography (HPLC) at UF. These data revealed that after an injection of 100 mg/kg, peak drug levels were 21.5+/−2.3 uM; the circulating half-life was 2.2+/−0.2 hrs.

Studies of Myelination in Newborn Mice in Normoxia

Figure 3:
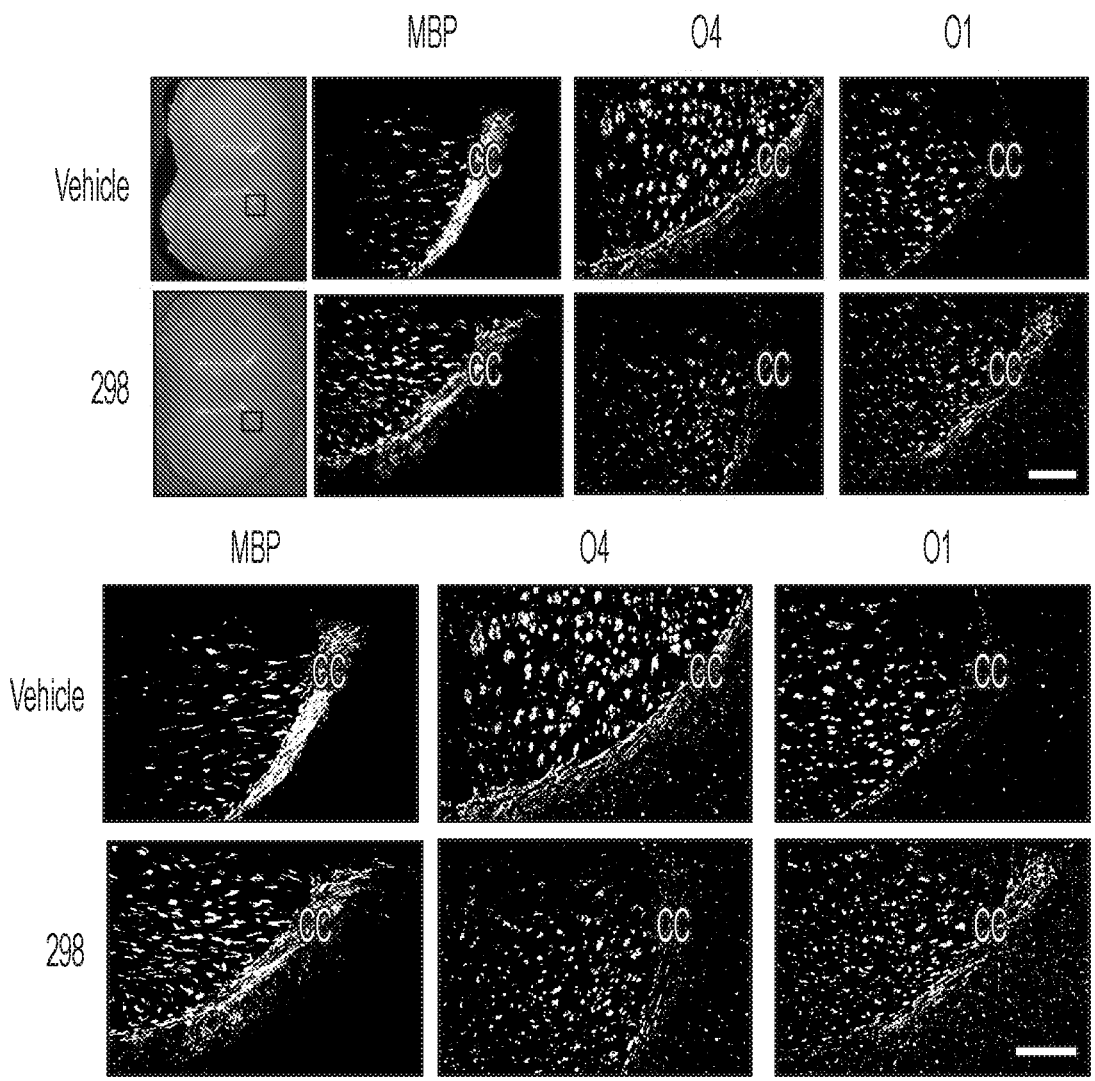
FIG. 3. depicts results of studies of myelination in newborn mice in normoxia.

After adult studies, pups were studied at developmental stages equivalent to preterm infants to assess effects on myelination, as reported by us[54]. C57BL/6 mice were reared in room air from P2 to P12, and treated daily with the compound or vehicle. In our studies of diazoxide in room air, we observed increased myelination[54]. K261-0298 (100 mg/kg) was given by injection, as above. Tissue slices were stained for markers of myelination (MBP) and oligodendrocyte development (O1, O4), as reported by us[29,55] This analysis revealed 27+/−4% increase in MBP labeling, a 44+/−4% decrease in O4 labeling, and a 26+/−5% increase in O1 labeling vs. vehicle (n=6; p<0.02; ANOVA; FIG. 3). These data suggest that there is increased maturation of oligodendrocyte lineage favoring the development of O1-positive myelinating oligodendrocytes. The fact that we observed changes in central nervous system myelination at animals at stages equivalent to preterm infants suggests that there is bioavailability of the compound to the brain, supporting the notion of penetration of the blood-brain-barrier of the compound.

Effects on Myelination in an Animal Model of White Matter Injury

Figure 4:
FIG. 4. Depicts results of studies of myelination in an animal model of white matter injury.

Data indicate that K261-0298 is useful to treat and/or prevent PWMI. We have initiated preclinical testing using the chronic sublethal hypoxia model of PWMI. Mice were reared under hypoxic or normoxic conditions from P2 to P12, as reported 64. At P2, litters were placed in a Plexiglas chamber in which ambient $O_2$ levels are maintained at 10.0±0.3% $O_2$. Normoxic animals were exposed to room air. To date we tested K261-0298 at 100 mg/kg, and mice were treated once per day from P2 to P12. At the end of the treatment period mice were examined for ventriculomegaly, as reported[64,65]. These data revealed a marked reduction in ventriculomegaly in the K261-0298 (0.0054+/−0.00013 m$^2$) vs. vehicle-treated (0.0156+/−0.0039 m$^2$) mice (n=4 per treatment, p<0.03; FIG. 4). Compared with normoxic controls[64,66], ventricle sizes in the drug-treated hypoxia animals were similar.

Summary of Supporting Data: Collectively, our data show that we identified compounds that are non-toxic, have favorable pharmacokinetic properties, promote the development of myelinating oligodendrocytes, and stimulate myelination in vivo and in vitro. As such, we are in a favorable position to pursue the development of compounds as novel therapeutics for a huge unmet need.

REFERENCES

1. Back S A. Perinatal white matter injury: the changing spectrum of pathology and emerging insights into pathogenetic mechanisms. Ment Retard Dev Disabil Res Rev 2006; 12:129-40.
2. Kinney H C, Back S A. Human oilgodendroglial development: relationship to periventricular leukomalacia. Seminars Pediatric Neurology 1988; 5:180-9.
3. Volpe J J. Neurobiology of periventricular leukomalacia in the premature infant. Pediatr Res 2001; 50:553-62.
4. Kuban K, Sanocka U, Leviton A, et al. White matter disorders of prematurity: association with intraventricular hemorrhage and ventriculomegaly. The Developmental Epidemiology Network. J Pediatr 1999; 134:539-46.
5. Salmaso N, Jablonska B, Scafidi J, Vaccarino F M, Gallo V. Neurobiology of premature brain injury. Nature neuroscience 2014; 17:341-6.
6. Back S A, Rosenberg P A. Pathophysiology of glia in perinatal white matter injury. Glia 2014.
7. Back S A, Miller S P. Brain injury in premature neonates: A primary cerebral dysmaturation disorder? Annals of neurology 2014; 75:469-86.
8. Dimitropoulos A, McQuillen P S, Sethi V, et al. Brain injury and development in newborns with critical congenital heart disease. Neurology 2013; 81:241-8.
9. Buser J R, Maire J, Riddle A, et al. Arrested preoligodendrocyte maturation contributes to myelination failure in premature infants. Annals of neurology 2012; 71:93-109.
10. Back S A. White matter injury in the preterm infant: pathology and mechanisms. Acta Neuropathol 2017.
11. Wilson-Costello D, Friedman H, Minich N, Fanaroff A A, Hack M. Improved survival rates with increased neurodevelopmental disability for extremely low birth weight infants in the 1990s. Pediatrics 2005; 115:997-1003.
12. Volpe J J. Brain injury in premature infants: a complex amalgam of destructive and developmental disturbances. Lancet Neurol 2009; 8:110-24.
13. Edgin J O, Inder T E, Anderson P J, Hood K M, Clark C A, Woodward U. Executive functioning in preschool children born very preterm: relationship with early white matter pathology. J Int Neuropsychol Soc 2008; 14:90-101.
14. Woodward L J, Edgin J O, Thompson D, Inder T E. Object working memory deficits predicted by early brain injury and development in the preterm infant. Brain 2005; 128:2578-87.
15. Bayless S, Stevenson J. Executive functions in school-age children born very prematurely. Early Hum Dev 2007; 83:247-54.
16. AIin M, Rooney M, Cuddy M, et al. Personality in young adults who are born preterm. Pediatrics 2006; 117:309-16.
17. AIin M, Walshe M, Fern A, et al. Cognitive maturation in preterm and term born adolescents. J Neurol Neurosurg Psychiatry 2008; 79:381-6.
18. Nosarti C, Giouroukou E, Healy E, et al. Grey and white matter distribution in very preterm adolescents mediates neurodevelopmental outcome. Brain 2008; 131:205-17.
19. Walshe M, Rifkin L, Rooney M, et al. Psychiatric disorder in young adults born very preterm: role of family history. Eur Psychiatry 2008; 23:527-31.
20. Constable R T, Ment L R, Vohr B R, et al. Prematurely born children demonstrate white matter microstructural differences at 12 years of age, relative to term control subjects: an investigation of group and gender effects. Pediatrics 2008; 121:306-16.
21. Kesler S R, Reiss A L, Vohr B, et al. Brain volume reductions within multiple cognitive systems in male preterm children at age twelve. J Pediatr 2008; 152:513-20, e1.
22. Thompson D K, Wood S J, Doyle L W, Warfield S K, Egan G F, Inder T E. MR-determined hippocampal asymmetry in full-term and preterm neonates. Hippocampus2009; 19:118-23.
23. Thompson D K, Wood S J, Doyle L W, et al. Neonate hippocampal volumes: prematurity, perinatal predictors, and 2-year outcome. Annals of neurology 55 2008; 63:642-51.
24. Limperopoulos C, Bassan H, Gauvreau K, et al. Does cerebellar injury in premature infants contribute to the high prevalence of long-term cognitive, learning, and behavioral disability in survivors? Pediatrics 2007; 120: 584-93.
25. Limperopoulos C, Soul J S, Gauvreau K, et al. Late gestation cerebellar growth is rapid and impeded by premature birth. Pediatrics 2005; 115:688-95.
26. Hoyert D L, Mathews T J, Menacker F, Strobino D M, Guyer B. Annual summary of vital statistics: 2004. Pediatrics 2006; 117:168-83.
27. Rushing S, Ment L R. Preterm birth: a cost benefit analysis. Semin Perinatol 2004; 28:444-50.
28. Back S A. Brain Injury in the Preterm Infant: New Horizons for Pathogenesis and Prevention. Pediatr Neurol 2015; 53:185-92.
29. Back S A, Craig A, Luo N L, et al. Protective effects of caffeine on chronic hypoxia-induced perinatal white matter injury. Annals of neurology 2006; 60:696-705.
30. Scafidi J, Hammond T R, Scafidi S, et al. Intranasal epidermal growth factor treatment rescues neonatal brain injury. Nature 2014; 506:230-4.
31. Back S A, Luo N L, Borenstein N S, Levine J M, Volpe J J, Kinney H C. Late oligodendrocyte progenitors coincide with the developmental window of vulnerability for human perinatal white matter injury. J Neurosci 2001; 21:1302-12.
32. Rezaie P, Dean A. Periventricular leukomalacia, inflammation and white matter lesions within the developing nervous system. Neuropathology 2002; 22:106-32.
33. Perlman J M. White matter injury in the preterm infant: an important determination of abnormal neurodevelopment outcome. Early Hum Dev 1998; 53:99-120.
34. van Tilborg E, de Theije C G M, van Hal M, et al. Origin and dynamics of oligodendrocytes in the developing brain: Implications for perinatal white matter injury. Glia 2018; 66:221-38.
35. van Tilborg E, Heijnen C J, Benders M J, et al. Impaired oligodendrocyte maturation in preterm infants: Potential therapeutic targets. Prog Neurobiol 2016; 136:28-49.
36. Back S A. Cerebral white and gray matter injury in newborns: new insights into pathophysiology and management. Clinics in perinatology 2014; 41:1-24.
37. Back S A, Rivkees S A. Emerging concepts in periventricular white matter injury. Semin Perinatol 2004; 28:405-14.
38. Back S A, Gan X, Li Y, Rosenberg P A, Volpe J J. Maturation-dependent vulnerability of oligodendrocytes to oxidative stress-induced death caused by glutathione depletion. J Neurosci 1998; 18:6241-53.
39. Craig A, Ling Luo N, Beardsley D J, et al. Quantitative analysis of perinatal rodent oligodendrocyte lineage progression and its correlation with human. Experimental neurology 2003; 181:231-40.
40. Scolding N J, Rayner P J, Compston D A. Identification of A2B5-positive putative oligodendrocyte progenitor cells and A2B5-positive astrocytes in adult human white matter. Neuroscience 1999; 89:1-4.
41. Gard A L, Pfeiffer S E. Two proliferative stages of the oligodendrocyte lineage (A2B5+O4- and O4+GalC-) under different mitogenic control. Neuron 1990; 5:615-25.
42. Warrington A E, Barbarese E, Pfeiffer S E. Stage specific, (O4+GalC-) isolated oligodendrocyte progenitors produce MBP+myelin in vivo. Dev Neurosci 1992; 14:93-7.
43. Warrington A E, Pfeiffer S E. Proliferation and differentiation of O4+50 oligodendrocytes in postnatal rat cerebellum: analysis in unfixed tissue slices using anti-glycolipid antibodies. J Neurosci Res 1992; 33:338-53.
44. Skoff R P, Ghandour M S, Knapp P E. Postmitotic oligodendrocytes generated during postnatal cerebral development are derived from proliferation of immature oligodendrocytes. Glia 1994; 12:12-23.
45. Nishiyama A, Lin X H, Giese N, Heldin C H, Stallcup W B. Co-localization of NG2 proteoglycan and PDGF alpha-receptor on O2A progenitor cells in the developing rat brain. J Neurosci Res 1996; 43:299-314.
46. Ment L R, Schwartz M, Makuch R W, Stewart W B. Association of chronic sublethal hypoxia with ventriculomegaly in the developing rat brain. Brain ResearchDevelopmentalBrain Research 1998; 111:197-203.
47. Uehara H, Yoshioka H, Kawase S, et al. A new model of white matter injury in neonatal rats with bilateral carotid artery occlusion. Brain Res 1999; 837:213-20.
48. Back S A, Luo N L, Montine T J, Frei B, Murdoch G H. Human oligodendrocyte progenitors are vulnerable in periventricular leukomalacia. Ann Neurol 2002; 52:S112.
49. Back S A, Luo N L, Borenstein N S, Volpe J J, Kinney H C. Arrested oligodendrocyte lineage progression during human cerebral white matter development: dissociation between the timing of progenitor differentiation and myelinogenesis. J Neuropathol Exp Neurol 2002; 61:197-211.
50. Back S A. Recent advances in human perinatal white matter injury. In: Castellano-Lopez B, Nieto-Sampedro M, eds. Prog Brain Res. Amsterdam: Elsevier; 2001:131-47.
51. Segovia K N, McClure M, Moravec M, et al. Arrested oligodendrocyte lineage maturation in chronic perinatal white matter injury. Annals of neurology 2008; 63:520-30.
52. Riddle A, Dean J, Buser J R, et al. Histopathological correlates of magnetic resonance imaging-defined chronic perinatal white matter injury. Annals of neurology 2011; 70:493-507.
53. Zhu Y, Wendler C C, Shi 0, S. A. R. Diazoxide Promotes Oligodendrocyte Differentiation in Chronic Sublethal Hypoxia. Brain Res 2014; (in press).
54. Fogal B, McClaskey C, Yan S, Yan H, Rivkees S A. Diazoxide promotes oligodendrocyte precursor cell proliferation and myelination. PloS one 2010; 5:e10906.
55. Zhu Y, Wendler C C, Shi O, Rivkees S A. Diazoxide promotes oligodendrocyte differentiation in neonatal brain in normoxia and chronic sublethal hypoxia. Brain Res 2014; 1586:64-72.
56. U.S. Food and Drug Administration. Proglycem (diazoxide): Drug Safety Communication—Reports of Pulmonary Hypertension in Infants and Newborns. http://www.fda.gov/Safety/MedWatch/SafetyInformation/SafetyAlertsforHumanMedic alProducts/ucm455125.htm 2015.
57. Yan H, Rivkees S A. Hepatocyte growth factor stimulates the proliferation and migration of oligodendrocyte precursor cells. J Neurosci Res 2002; 69:597-606.
58. Dugas J C, Tai Y C, Speed T P, Ngai J, Barres B A. Functional genomic analysis of oligodendrocyte differentiation. J Neurosci 2006; 26:10967-83.
59. Yan H, Rivkees S A. Hypoglycemia influences oligodendrocyte development and myelin formation. Neuroreport 2005; (in press).
60. Othman T, Yan H, Rivkees S A. Oligodendrocytes express functional A1 adenosine receptors that stimulate cellular migration. Glia 2003; 44:166-72.

61. Jones L J, Gray M, Yue S T, Haugland R P, Singer V L. Sensitive determination of cell number using the CyQUANT cell proliferation assay. J Immunol Methods 2001; 254:85-98.
62. Murata A, Agematsu K, Korotcova L, Gallo V, Jonas R A, Ishibashi N. Rodent brain slice model for the study of white matter injury. The Journal of thoracic and cardiovascular surgery 2013; 146:1526-33 e1.
63. Yan H, Rivkees S A. Hypoglycemia influences oligodendrocyte development and myelin formation. Neuroreport 2006; 17:55-9.
64. Turner C P, Seli M, Ment L, et al. A1 adenosine receptors mediate hypoxia-induced ventriculomegaly. Proceedings of the National Academy of Sciences of the United States of America 2003; 100:11718-22.
65. Turner C P, Yan H, Schwartz M, Othman T, Rivkees S A. A1 adenosine receptor activation induces ventriculomegaly and white matter loss. Neuroreport 2002; 13:1199-204.
66. Turner C, Yan H, Schwartz M, Othman T, Rlvkees S. A1 adenosine receptor activation induces ventriculomegaly and white matter loss. Neuroreport 2002; 13:1199-204.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:
1. A compound of Formula I:

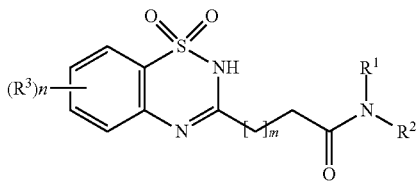

or pharmaceutically acceptable salt thereof, wherein:
each $R^1$ is independently H, alkyl substituted with 1-3 independent $R^4$;
each $R^2$ is independently alkyl substituted with 1-3 independent $R^4$; or
$R^1$ and $R^2$ taken together with the nitrogen atom to which they are attached form a heterocycloalkyl ring having 1, 2, or 3 heteroatoms selected from N, O, and S, wherein the heterocycloalkyl ring may be optionally substituted with 1-3 independent $R^4$;
each $R^3$ is independently alkyl, alkoxy, amino, halo, $C(O)R^5$, $C(O)OR^5$, $SR^5$, or $NR^5R^6$;
each $R^4$ is independently alkoxy, or aryl optionally substituted with 1-3 independent $R^7$;
each $R^5$ is independently H, or alkyl;
each $R^6$ is independently H, or alkyl;
each $R^7$ is independently alkyl, alkoxy, amino, halo, $C(O)R^5$, $C(O)OR^5$, $SR^5$, $S(O)_2R^5$, $S(O)_2NR^5R^6$, or $NR^5R^6$;
n is 0, 1, 2, 3, or 4; and
m is 1, 2, 3, or 4.

2. The compound of claim 1 of Formula I, or pharmaceutically acceptable salt thereof, wherein:
each $R^1$ is independently H;
each $R^2$ is independently alkyl substituted with 1-3 independent $R^4$;
n is 0, and m is 1.

3. The compound of claim 1 of Formula I, or pharmaceutically acceptable salt thereof, wherein:
each $R^1$ is independently H;
each $R^2$ is independently alkyl substituted with 1-3 independent $R^4$;
n is 0, and m is 1; and
each $R^4$ is independently alkoxy.

4. The compound of claim 1 of Formula I, or pharmaceutically acceptable salt thereof, wherein:
each $R^1$ is independently H;
each $R^2$ is independently alkyl substituted with 1-3 independent $R^4$;
n is 0, and m is 2.

5. The compound of claim 1 of Formula I, or pharmaceutically acceptable salts thereof, wherein:
each $R^1$ is independently H;
each $R^2$ is independently alkyl substituted with 1-3 independent $R^4$;
n is 0, and m is 2;
each $R^4$ is independently alkoxy.

6. The compound of claim 1 of Formula I, or pharmaceutically acceptable salt thereof, wherein:
$R^1$ and $R^2$ taken together with the nitrogen atom to which they are attached form a heterocycloalkyl ring having 1 or 2 heteroatoms selected from N, O, and S, wherein the heterocycloalkyl ring may be optionally substituted with with 1-3 independent $R^4$;
n is 0, and m is 1.

7. The compound of claim 1 of Formula I, or pharmaceutically acceptable salt thereof, wherein:
$R^1$ and $R^2$ taken together with the nitrogen atom to which they are attached form a heterocycloalkyl ring having 1 or 2 heteroatoms selected from N, O, and S, wherein the heterocycloalkyl ring may be optionally substituted with 1-3 independent $R^4$;
n is 0, and m is 1;
each $R^4$ is independently aryl optionally substituted with 1-3 independent $R^7$;
each $R^7$ is independently alkyl, alkoxy, amino, halo, $C(O)R^5$, $C(O)OR^5$, $SR^5$, $S(O)_2R^5$, $S(O)_2NR^5R^6$, or $NR^5R^6$.

8. The compound of claim 1 of Formula I, or pharmaceutically acceptable salt thereof:
wherein n is 0, and m is 1;
wherein n is 0, and m is 2.

9. The compound of claim 1, that is:

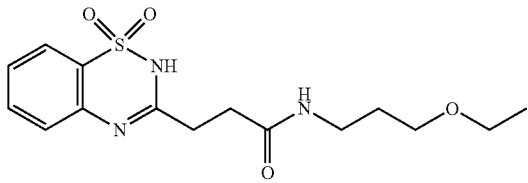

K261-0298
3-(1,1-dioxido-2H-benzo[e][1,2,4]thiadiazin-3-yl)-N-(3-ethoxypropyl)propanamide

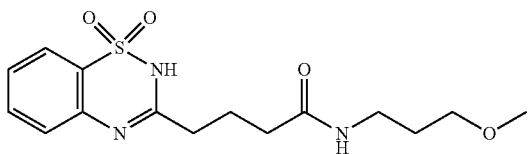

K261-0186
4-(1,1-dioxido-2H-benzo[e][1,2,4]thiadiazin-3-yl)-N-(3-methoxypropyl)butanamide

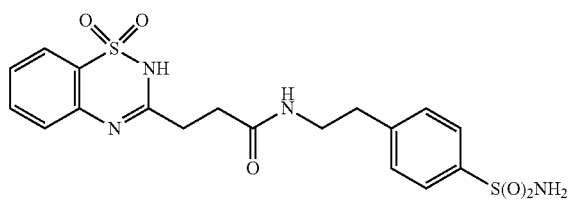

K261-0288
3-(1,1-dioxido-2H-benzo[e][1,2,4]thiadiazin-3-yl)-N-(4-sulfamoylphenethyl)propanamide -continued

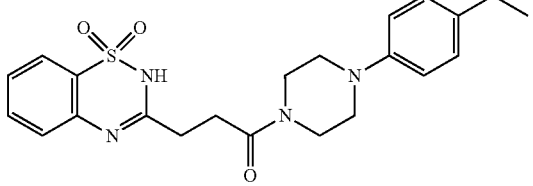

K261-0310
1-(4-(4-acetylphenyl)piperazin-1-yl)-3-(1,1-dioxido-2H-benzo[e][1,2,4]thiadiazin-3-yl)propane-1-one or a pharmaceutically acceptable salt thereof.

10. A pharmaceutical composition comprising a compound of any of claims 1-9, or pharmaceutically acceptable salt thereof and a pharmaceutically acceptable carrier.

11. A method of stimulating myelination (e.g., treating hypomyelination), comprising administering to a subject in need thereof, an effective amount of a compound or pharmaceutical composition of any of claims 1-10, or pharmaceutically acceptable salt thereof.

12. A method of stimulating proliferation of oligodendrocytes (OLs) or stimulating oligodendrocyte precursor cells, comprising administering to a subject in need thereof, an effective amount of a compound of Formula I in any of claims 1-9, or pharmaceutically acceptable salt thereof, or pharmaceutical composition thereof of claim 10.

13. A method of reducing ventriculomegaly, comprising administering to a subject in need thereof, an effective amount of a compound of Formula I in any of claims 1-9, or pharmaceutically acceptable salt thereof, or pharmaceutical composition thereof of claim 10.

* * * * *